United States Patent [19]
Sendo et al.

[11] Patent Number: 5,539,102
[45] Date of Patent: Jul. 23, 1996

[54] PRODUCTION METHOD FOR SULFAMIDE

[75] Inventors: Yuji Sendo, Itami; Makoto Kii, Amagasaki; Yasuhiro Nishitani, Izumi; Tadashi Irie, Suita; Yutaka Nishino, Neyagawa, all of Japan

[73] Assignee: Shionogi Seiyaku Kabushiki Kaisha, Osaka, Japan

[21] Appl. No.: 19,105

[22] Filed: Feb. 18, 1993

[30] Foreign Application Priority Data

Feb. 21, 1992 [JP] Japan .................................. 4-035366
Jul. 8, 1992 [JP] Japan .................................. 4-180930
Aug. 20, 1992 [JP] Japan .................................. 4-221767

[51] Int. Cl.$^6$ .................................................. C07D 499/00
[52] U.S. Cl. .......................... 540/310; 540/215; 540/312; 540/222; 540/350; 548/544; 548/552
[58] Field of Search .................................. 540/312, 310, 540/215, 222, 350, 310; 548/544, 552

[56] References Cited

FOREIGN PATENT DOCUMENTS 0050927 5/1982 European Pat. Off. .

OTHER PUBLICATIONS

Osikawa et al, "Dialkyl Phosphonate–Promoted Reaction of Alcohols With Diethyl Azodicarboxylate and Triphenylphosphine: Preparation of Diethyl 1–Substituted–1, 2–Hydrazinedicarboxylate", Shizuoka Daigaku, Kogakubu Kenkyu Hokoku 1984, 35. 37–40, Chem Abstract 103: 142095d.

Grynkrewicz et al, "Reaction of 1,2:3,4–di–O–Usopropylidene–alpha–D–Galactopyranose With Dialkyl Azodicarboxylate in the Presence of Triphenylphosphine". Bulletin De L'Academie Polonaise Des Sciences, Series. des Sciences Chimiques, vol. XXIV, No. 2, 1976, Chem. Abstract 85:333 13n.

Chemical Abstracts vol. 120:133875 (1994).
Chemical Abstracts vol. 118:255277 (1993).

C. H. Lee et al, *J. Org. Chem.*, vol. 55, No. 25, 1990, pp. 6098–6104, "Intra–and Intermolecular alpha–Sulfamidoalkylation Reactions".

A. Giraldez et al, *Eur. J. Med. Chem.* 24, 1989, pp. 497–502, "Analgesic and Antipyretic Activities of 1,2,6–thiadiazin 3 one, 1,1 dioxides. SAR design of a new analgesic agent".

G. W. Muller et al, *J. Org. Chem.* vol. 54, No. 18, 1989, pp. 4471–4473 "A General Synthesis of 4–Substituted 1,1–Dioxo–1,2,5–Thiadiazolidin–3–ones Derived from alpha–amino Acids".

B. Unterhalt et al, *Arch. Pharm. (Weinheim) 321*, 375–376, 1988, "2,4–Disubstituierte 3–Oxo–1,2,5–thiadiazolidin 1,1 dioxide".

C. H. Lee et al, *Journal of Pharmaceutical Sciences*, vol. 79, No. 8, Aug. 1990, pp. 716–718 "Anticonvulsant Properties of 3–Oxo–and 3–lmino–4–substituted 1,2,5–thiadiazolidine 1,1–Dioxides".

*Primary Examiner*—Nicholas Rizzo
*Attorney, Agent, or Firm*—Renner, Otto, Boisselle & Sklar

[57] ABSTRACT

The method for producing a sulfamide according to the present invention includes the step of reacting an alcohol and an oxycarbonylsulfamide compound in the presence of a trivalent phosphorus compound and an azodicarboxylic acid derivative. In one embodiment, the sulfamide is represented by Formula I, the alcohol is represented by Formula II, and the oxycarbonylsulfamide compound is represented by Formula III:

$$R^3NHSO_2NR^1R^2 \qquad (I)$$

wherein $R^1$ and $R^2$ are independently selected from the group consisting of hydrogen, alkyl, cycloalkyl, alkenyl, alkynyl, aralkyl, aryl, a heterocyclic group, and alkyl substituted with the heterocyclic group, respectively, said heterocyclic group being selected from the group consisting of pyranosyl, furanosyl, piperidinyl, pyrrolidinyl, an azetidinone ring, a cephem ring, a penem ring, and a carbapenem ring; $R^3$ is selected from the group consisting of alkyl, alkenyl, alkynyl, aralkyl, a heterocyclic group, alkyl substituted with the heterocyclic group, and pyrrolidinylmethyl, said heterocyclic group being selected from the group consisting of pyranosyl, furanosyl, piperidinyl, pyrrolidinyl, an azetidinone ring, a cephem ring, a penem ring, and a carbapenem ring;

$$R^3OH \qquad (II)$$

wherein $R^3$ is defined as above;

$$R^4OOC-NHSO_2NR^1R^2 \qquad (III)$$

wherein $R^1$ and $R^2$ are defined as above; and $R^4$ is a carboxy protecting group.

17 Claims, No Drawings

PRODUCTION METHOD FOR SULFAMIDE

BACKGROUND OF THE INVENTION

1. Field of the Invention

The present invention relates to a production method of sulfamides which are useful for producing medicaments, medicines for plants and animals, polymers and stereoisomer alcohol compounds.

2. Description of the Related Art

The production of sulfamides from alcohol generally includes 4 to 5 steps: Alcohol is converted into a halogen compound or sulfonyl ester, the halogen or the sulfonyl ester group is substituted with an azido group to obtain an azide compound, and the azido group is reduced to an amino group. Alternatively, alcohol is converted into a halogen compound or sulfonyl ester, the halogen or the sulfonyl ester group is substituted with a phthalimido group, and a phthaloyl group in the phthalimido group is removed with hydrazine to obtain an amino group. The amine produced in either of the above described methods is reacted with a sulfamoylating agent, thereby obtaining a sulfamide. The resultant sulfamide is deprotected, if necessary.

This method has the following problems: the abovementioned steps are complicated; it is necessary to introduce or remove a protecting group which is adaptable to the reaction condition in each step when the compound to be reacted has a functional group which may generate a side reaction in its molecule; and the azide compound and hydrazine, which are highly explosive and toxic, are required.

SUMMARY OF THE INVENTION

The method for producing a sulfamide of this invention comprises the step of reacting an alcohol and an oxycarbonylsulfamide compound in the presence of a trivalent phosphorus compound and an azodicarboxylic acid derivative.

In one embodiment, the sulfamide is represented by Formula I, the alcohol is represented by Formula II, and the oxycarbonylsulfamide compound is represented by Formula III:

$$R^3NHSO_2NR^1R^2 \quad (I)$$

wherein $R^1$ and $R^2$ are independently selected from the group consisting of hydrogen, alkyl, cycloalkyl, alkenyl, alkynyl, aralkyl, aryl, a heterocyclic group, and alkyl substituted with the heterocyclic group, respectively, said heterocyclic group being selected from the group consisting of pyranosyl, furanosyl, piperidinyl, pyrrolidinyl, an azetidinone ring, a cephem ring, a penem ring, and a carbapenem ring $R^3$ is selected from the group consisting of alkyl, alkenyl, alkynyl, aralkyl, a heterocyclic group, alkyl substituted with the heterocyclic group, and pyrrolidinylmethyl, said heterocyclic group being selected from the group consisting of pyranosyl, furanosyl, piperidinyl, pyrrolidinyl, an azetidinone ring, a cephem ring, a penem ring, and a carbapenem ring;

$$R^3OH \quad (II)$$

wherein $R^3$ is defined as above;

$$R^4OOC-NHSO_2NR^1R^2 \quad (III)$$

wherein $R^1$ and $R^2$ are defined as above; and $R^4$ is a carboxy protecting group.

In another embodiment, the method further comprises the step of removing $-COOR^4$.

Thus, the invention described herein makes possible the advantages of (1) providing a production method for a sulfamide comprising two steps of a condensation reaction and a deprotection reaction both of which can be conducted under a mild and neutral condition, which requires 4 to 5 steps in conventional methods; (2) providing a simple method for producing sulfamides useful as materials for synthesizing physiologically active materials such as antibacterial agents, antipyretics, analgesics, sweetners, sleeping agents and anticonvulsants; and (3) providing a method for producing such sulfamides in a high yield.

These and other advantages of the present invention will become apparent to those skilled in the art upon reading and understanding the following detailed description.

DESCRIPTION OF THE PREFERRED EMBODIMENTS

The following are abbreviations used herein:

Ac: acetyl

Boc: t-butoxycarbonyl

Bz: benzene

DCM: dichloromethane

EtOAc: ethyl acetate

Et: ethyl

Me: methyl

PMB: p-methoxybenzyl

PNB: p-nitrobenzyl

Ph: phenyl

THF: tetrahydrofuran

To: toluene t-Bu: t-butyl

In the production method for sulfamides (I) according to the present invention, an alcohol (II) and an oxycarbonylsulfamide compound (III) are reacted in the presence of a trivalent phosphorus compound and an azodicarboxylic acid derivative.

The method of the present invention is exemplified by the following scheme:

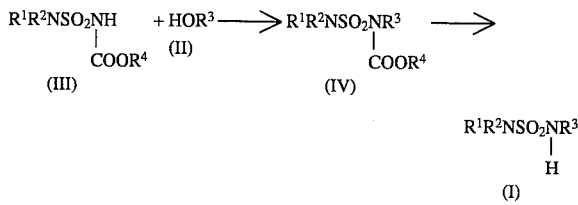

wherein $R^1$ and $R^2$ are, for example, one independently selected from the group consisting of hydrogen, alkyl, cycloalkyl, alkenyl, alkynyl, aralkyl, aryl, a heterocyclic group such as pyranosyl, furanosyl, piperidinyl, pyrrolidinyl, an azetidinone ring, a caphem ring, a penem ring and a carbapenem ring, and alkyl substituted with such a heterocyclic group, respectively; $R^3$ is, for example, one selected from the group consisting of alkyl, alkenyl, alkynyl, aralkyl, a heterocyclic group such as pyranosyl, furanosyl, piperidinyl, pyrrolidinyl, an azetidinone ring, a cephem ring, a penem ring and a carbapenem ring, and alkyl substituted with the heterocyclic group, and $R^3$ is preferred to be pyrrolidinylmethyl; and $R^4$ is a carboxy protecting group.

The method will now be described concretely. An oxycarbonylsulfamide compound (III), a trivalent phosphorus compound end an azodicarboxylic acid derivative are added to an alcohol (II) in an inert aprotic solvent. The mixture is allowed to react, preferably at a temperature of −70° C. to +50° C. for 0.5 to 20 hours, to obtain an oxycarbonylsulfamide compound (IV). If necessary, $R^4OOC$ is removed from the obtained product in a usual manner to give a sulfamide compound (I).

A preferred scope of each component used in the present invention is as follows:

Examples of the amino substituents $R^1$ end $R^2$ in the oxycarbonylsulfamide compound ($R^4OOCNHSO_2NR^1R^2$) (I) include hydrogen, alkyl, cycloalkyl, alkenyl, alkynyl, aralkyl, aryl, heterocyclic groups such as pyranosyl, furanosyl, piperidinyl, pyrrolidinyl, an azetidinone ring, a caphem ring, a penem ring and a carbapenem ring, and alkyl substituted with a heterocyclic group, e.g., pyrrolidinylmethyl. $R^1$ and $R^2$ can be the same or different substituents. Examples of the carboxy protecting group $R^4$ include alkyl, alkenyl, alkynyl, aralyl and aryl, and preferably an easily removable carbonate ester forming group.

The group $R^3$ in the alcohol ($R^3OH$) (II) herein is a carbon containing group, and the examples include alkyl, alkenyl, alkynyl, aralkyl, heterocyclic groups such as pyranosyl, furanosyl, piperidinyl, pyrrolidinyl, an azetidinone ring, a caphem ring, a penem ring and a carbapenem ring, alkyl substituted with the heterocyclic group, and especially, pyrrolidinylmethyl, all of which can contain a substituent. The substituent is a group which does not inhibit the reaction such as alkyl, acyl, acyloxy, alkoxy, sulfonyl, sulfonyloxy, an esterified phosphoric acid group and halogens. Examples of the alcohol herein include primary, secondary and tertiary alcohols, but the above-mentioned primary alcohols are preferred because of their high reactivity.

Examples of the trivalent phosphorus compound herein include trialkylphosphines such as triethylphosphine and tributylphosphine; triarylphosphines such as triphenylphosphine and tritolylphosphine; and phosphites such as methyl phosphite, ethyl phosphite, and phenyl phosphite.

Examples of the azodicarboxylic acid derivative herein include alkyl azodicarboxylates such as methyl azodicarboxylate, ethyl azodicarboxylate and isopropyl azodicarboxylate; azodinitrile; azodicarboxamide; bisdialkylamides of azodicarboxylic acid such as bisdimethylamide of azodicarboxylic acid and bisdiethylamide of azodicarboxylic acid; 1,1'-(azodicarbonyl)dialkyleneamines such as 1,1'-(azodicarbonyl)dipyrrolidine and 1,1'-(azodicarbonyl)dipiperidine.

The alkyl moiety in each of the above-mentioned compounds is linear, branched or cyclic alkyl, typically an alkyl group having 1 to 12 carbon atoms. Such cyclic alkyl can contain one or more hetero atoms such as oxygen, nitrogen and sulfur in its ring structure. Examples of the alkyl moiety include methyl, ethyl, propyl, isopropyl, cyclopropyl, butyl, isobutyl, tertiary butyl, cyclobutyl, cyclopropylmethyl, pyrrolidinyl, pentyl, isopentyl, neopentyl, cyolopentyl, cyclopropylethyl, piperidyl, hexyl, cyclohexyl, cyclopentylmethyl, heptyl, cycloheptyl, cyclopentylethyl, cyclohexylmethyl, octyl, cyclooctyl, cyclohexylethyl, nonyl and dodecyl, all of which can contain a substituent described below.

The alkenyl moiety or the alkynyl moiety in each of the above-mentioned compounds is the alkyl moiety which has one or more unsaturated bonds in its structure, and can contain a substituent described below.

The aralkyl moiety in each of the above-mentioned compounds has a structure of a combination of the alkyl moiety and the aryl moiety, and is typically an aralkyl group having 7 to 14 carbon atoms. The examples include benzyl, phenetyl, phenylpropyl, phenylisopropyl, diphenylmethyl, methoxydiphenylmethyl, naphtylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl and quinolylmethyl, all of which can have a substituent described below.

The acyl moiety in each of the above-mentioned compounds includes a carboxylic aciyl group having 14 or less of carbon atoms such as linear, branched or cyclic alkanoyl; mono-cyclic or bicyclic aroyl, aralkanoyl and arylalkenoyl which can contain a hetero atom; a sulfonic acyl group having 14 or less of carbon atoms such as alkylsulfonyl, arylsulfonyl; a carbonic acyl group having 14 or less of carbon atoms such as alkoxycarbonyl, aralkoxycarbonyl, and carbamoyl; a phosphoric acyl group having 14 or less of carbon atoms such as phenylphosphoryl; and a sulfuric acyl group, i.e. sulfo. The above-mentioned acyl moiety can contain a substituent described below.

When each of the above groups has a substituent, the above-mentioned carbon numbers do not include a carbon number of the substituent.

Examples of the substituent which can be bonded to each of the above-mentioned groups include carbon functional groups having 10 or less carbon atoms such as linear, branched or cyclic alkyl, alkenyl, alkynyl, aralkyl, aryl, carboxylic acyl, carbamoyl, protected carboxy and cyano; nitrogen functional groups such as amino, acylamino, guanidyl, ureido, alkylamino, dialkylamino, isothiocyano, isocyano, nitro and nitroso; oxygen functional groups such as alkoxy, aryloxy, cyanato, oxo, carboxylic acyloxy, sulfonic acyloxy and phosphoric acyloxy; sulfur functional groups such as alkylthio, alkylsulphonyl, arylthio, arylsulphonyl, acylthio, thioxo, sulfo and sulfamoyl; halogens such as fluorine, chlorine, bromine and iodine; silyl groups such as trialkylsilyl and dialkylalkoxysilyl; and stannyl groups such as trialkylstannyl.

When a compound used as a starting material for producing a sulfamide by the method of the present invention has, in its molecule, a functional group which can cause a side reaction, the functional group can be protected by a usual method, and then deprotected by a usual method after the condensation reaction is carried out.

Preferred reaction conditions of the present invention are as follows:

The above-mentioned condensation and deprotection reactions are generally conducted at a temperature of −80° C. to +100° C., preferably at −70° C. to +50° C., for 10 minutes to 25 hours, preferably for 0.5 to 20 hours. The product which is stable in the reaction solution can be allowed to stand for a longer period. In the condensation reaction, preferably, 1 to 5 equivalents of the oxycarbonylsulfamide compound (I), 1 to 5 equivalents of the trivalent phosphorus compound and 1 to 5 equivalents of the azodicarboxylic acid derivative are reacted with 1 equivalent of the alcohol (II). Any of the following solvents can be used in these reactions: hydrocarbons such as pentane, hexane, octane, benzene, toluene and xylene; halogenated hydrocarbons such as dichloromethane, chloroform, carbon tetrachloride, dichloroethane, trichloroethane and chlorobenzene; ethers such as diethylether, methylisobutylether, dioxane and tetrahydrofurane; ketones such as acetone, methylethylketone and cyclohexanone; esters such as ethyl acetate, isobutyl acetate and methyl benzoate; nitrogenated hydrocarbons such as nitromethane and nitrobenzene; nitriles such as acetnitrile and benzonitrile; amides such as formamide, acetamide, dimethylformamide, dimethylacetamide and hexamethylphophotriamide; sulfoxides such as dimethylsulfoxide; organic bases such as diethylamine, triethylamine, cyclohexylamine, benzylamine, pyridine, picoline, collidine and quinoline; and other types of inert industrial solvents or mixtures thereof. Especially, the reaction solvent used in the condensation reaction is preferably at least one selected from the group consisting of inert solvents such as tetrahydrofurane, dioxane, dichloromethane and ethyl acetate. Any of the above-mentioned reactions can be conducted, if necessary, under an anhydrous condition, by using an inert gas, and/or with stirring.

The objective product can be isolated by a usual post-treatment such as adsorption, elution, distillation, precipitation, deposition and chromatography after removing impurities such as an unreacted material, and a side reaction product and a solvent by a usual method such as extraction, evaporation, washing, concentration, precipitation, filtering, drying and the like.

The yield of the sulfamide according to the present invention is generally 50 to 90% when a primary alcohol is used as a starting material. The reactivity of the alcohols in the condensation reaction is degraded depending on the kind of the alcohols in the order of primary, secondary and tertiary alcohols.

As described above, according to the present invention, sulfamides are produced by a novel method in which alcohol and an oxicarbonylsulfamide compound are reacted in the presence of a trivalent phosphorus compound and an azodicarboxylic acid derivative, in order to proceed a condensation reaction under a mild and neutral condition. Synthesis of the sulfamide compounds, which requires 4 to 5 steps in the conventional procedure, is simplified to have only 2 steps, that is, the condensation reaction and the deprotection reaction, both of which can be conducted under a mild and neutral condition. Especially when a primary alcohol is used as a starting material, the objective sulfamide can be easily and effectively synthesized in a high yield.

The characteristics of the method according to the present invention are as follows:

1) The method is superior because a sulfamide can be derived from alcohol only in 2 steps.

2) The condensation reaction is proceeded under a mild and neutral condition.

3) When the alcohol has an optically active center, the condensation reaction proceeds stereospecifically, the reaction being $S_N2$ substituting reaction in which a configuration of the product is reversed with respect to the starting material, i.e., the alcohol. Therefore, this reaction is appropriate for obtaining a specific type of a stereoisomer.

(Usefulness of the Present Method)

The method of the present invention is characterized in that sulfamides are directly derived from alcohols, especially primary alcohols. Sulfamides are useful for preparing various physiologically active materials (C. H. Lee and H. Kohn, *J. Org. Chem.* 1990, 55, 6098), β-lactam antibacterial agents (Japanese Patent Application No. 3-207972), antipyretics, analgesics (A. Giraldes, R. Nieves, C. Ochoa, C. Vera de Ray, E. Cenarruzabeitia and B. Lasheras, *Eur. J. Med. Chem.* 1989, 24, 497), sweeteners (G. W. Muller and G. E. DuBois, *J. Org. Chem.*, 1989, 54, 4471), sleeping agents (B. Unterhalt and G. A. Hanewacker, *Arch. Pharm.* (Weinheim) 1988, 321, 375) and anticonvulsants (C. H. Lee and H. Kohn, *J. Pharm. Sci.*, 1990, 79, 716), because such materials and agents often have a sulfamide in their chemical structures. For example, (1R,5S,6S)-6-[(1R)-1-hydroxyethyl]-2[(3S,5S)-5-sulfamidomethylpyrrolidin-3-yl]thio-1-methyl-carba-2-penem3-carboxylic acid obtained in Reference Example 10 described below is a novel antibacterial agent showing a strong antibacterial activity against Gram-positive bacteria and Gram-negative bacteria. Moreover, the production method for sulfamides from alcohols according to the present invention is also used in chemical modifications of high molecular polyhydric alcohols and natural alcohol stereoisomers.

EXAMPLES

The present invention will now be described by way of examples.

Production Example: Synthesis of an oxycarbonylsulfamide compound

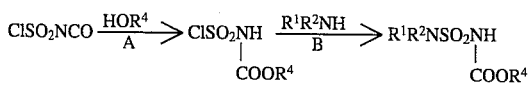

1) $R^1 = R^2 = H, R^4 = t$-Bu  4) $R^1 = Ph$  $R^2 = H$
   $R^4 = t$-Bu

2) $R^1 = R^2 = H, R^4 = PNB$  5) $R^1 = $
3) $R^1 = R^2 = H,$
   $R^4 = -CH_2CH=CH_2$

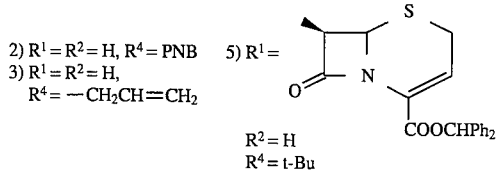

$R^2 = H$
$R^4 = t$-Bu

Step A: To a solution of alcohol ($R^4OH$) in a solvent is added dropwise chlorosulfonyl isocyanate ($ClSO_2NCO$) under reaction conditions as shown in Table 1. The mixture is stirred to give a solution of N-chlorosulfonylcarbamate. This solution can be used directly for the reaction of the next step.

TABLE 1

| | Synthesis of N-chlorosulfonylcarbamate (A) | | | | |
|---|---|---|---|---|---|
| Sample No. | $ClSO_2NCO$ (Eq.) | Solvent (vol.)*⁾ | Temp. (°C.) | Time (min.) | Yield (%) |
| 1 | 1.0 | EtOAc (21.1) | −40 → −18 | drop → 20 | cont.**⁾ |
| 2 | 1.0 | DCM (1.2) | −20 → rt. | 30 → 140 | 97 |
| 3 | 1.0 | DCM (2.9) | −35 → rt. | 10 → 200 | cont. |
| 4 | 1.0 | EtOAc (11.5) | −40 → −18 | 20 → 20 | cont. |
| 5 | 1.0 | EtOAc (10.6) | −35 → −20 | 25 → 20 | cont. |

Note:
*⁾A ratio of a solvent (ml) to an alcohol (g).
**⁾The reaction mixture is subjected to the following Step B without work up.

Step B: To a solution of N-chlorosulfonylcarbamate is added an amine ($R^1R^2NH$) under reaction conditions as shown in Table 2, and the mixture is stirred. The reaction mixture is neutralized and extracted with ethyl acetate. The extract is washed with water, dried, and concentrated in vacuo to give an oxycarbonylsulfamide compound.

TABLE 2

Synthesis of oxycarbonylsulfamide (B)

| Sample No. | Solvent (vol.)*) | $R^1R^2NH$ (Eq.) | Temp. (°C.) | Time (min.) | Yield (%) |
|---|---|---|---|---|---|
| 1 | cont.**) | 40 | −72 → rt. | 50 | 89 |
| 2 | THF (7.3) | 40 | −70 → 10 | 10 → 20 | 88 |
| 3 | cont. | 60 | −65 → 18 | 4 → 40 | 70 |
| 4 | cont. | 2.0 | −65 → −35 | 60 | 93 |
| 5 | cont. +NEt₃ (1.1) | 1.1 | −60 → −40 → 0 | 30 → 90 → 60 | 49 |

Note:
*) A ratio of a solvent (ml) to an alcohol (g).
**) The reaction mixture from Step A is subjected to Step B without work up.

Physical constants of the obtained products are as follows:
1) $R^1=R^2=H$, $R^4=$t-butyl
  mp. 130°–131° C.
  IR ν (Nujol) cm⁻¹: 3360, 3270, 1718, 1548.
  NMR δ (CD₃SOCD₃) 200 MHz ppm: 1.43(s, 9H), 7.27(s, 2H).
  Anal. ($C_5H_{12}N_2O_4S$) Calcd.: C, 30.60; H, 6.17; N, 14.28; S, 16.34. Found: C, 30.39; H, 6.11; N, 14.30; S, 16.30.
2) $R^1=R^2=H$, $R^4=$p-nitrobenzyl
  mp. 176°–177° C.
  IR ν (Nujol) cm⁻¹: 3345, 3215, 1718, 1346, 1153.
  NMR δ (CD₃SOCD₃) 200 MHz ppm: 5.30(s, 2H), 7.54(s, 2H), 7.65(d, J=8.6 Hz,2H), 8.27(d, J=8.6 Hz, 2H), 11.33(s, 1H).
  Anal. ($C_8H_9O_6N_3S$) Calcd.: C, 34.91; H, 3.29; N, 15.27; S, 11.65. Found: C, 35.00; H, 3.45; N, 15.33; S, 11.53.
3) $R^1=R^2=H$, $R^4=$allyl
  mp. 119°–121° C.
  IR ν (THF) cm⁻¹: 1745, 1377, 1160.
  NMR δ (CD₃SOCD₃) 200 MHz ppm: 4.59(dd, J₁=1.2 Hz, J₂=4.0 Hz, 2H), 5.20–5.39(m, 2H), 5.83–6.02(m, 1H), 7.45(s, 2H), 11.20(s, 1H).
  Anal. ($C_4H_8O_4N_2S$) Calcd.: C, 26.66; H, 4.47; N, 15.55; S, 17.79. Found: C, 26.79; H, 4.53; N, 15.51; S, 17.71.
4) $R^1=$phenyl, $R^2=H$, $R^4=$t-butyl
  mp. 147° C.
  IR ν (CHCl₃) cm⁻¹: 3246, 3190, 1699, 1356, 1141.
  NMR δ (CD₃SOCD₃) 200 MHz ppm: 1.33(s, 9H), 7.05–7.36(m, 4H), 10.25(s, 1H), 11.23(s, 1H).
  Anal. ($C_{11}H_{16}O_4N_2S$) Calcd.: C, 48.51; H, 5.92; N, 10.29; S, 11.77. Found: C, 48.36; H, 5.91; N, 10.38; S, 11.72.
5) $R^1=$(4-diphenylmethoxycarbonyl-3-cephem)-7-yl, $R^2=H$, $R^4=$t-butyl
  mp. 165°–166° C.
  IR ν (CHCl₃) cm⁻¹: 3390, 3300, 1795, 1735, 1371, 1145.
  NMR δ (CDCl₃) 200 MHz ppm: 1.52(s, 9H), 3.41, 3.52(d, ABq, $J_{AB}$=20 Hz, J₁=3.2 Hz, J₂=5.8 Hz), 4.93(d, J=5.4 Hz, 1H), 5.51(dd, J₁=5.4 Hz, J₂=10.6 Hz, 1H), 6.24(d, J=10.6 Hz, 1H), 6.63(dd, J₁=3.2 Hz, J₂=5.8 Hz, 1H), 6.92 (s, 1H), 7.20–7.50(m, 10H), 7.73(s, 1H).
  Anal. ($C_{25}H_{27}O_7N_3S_2$) Calcd.: C, 54.67; H, 5.03; N, 7.65; S, 11.67. Found: C, 54.68; H, 5.03; N, 7.80; S, 11.55.

[Condensation using a primary alcohol]

Example 1

(Using benzyl alcohol or thienylmethyl alcohol)

$$H_2NSO_2NH\underset{COOR^4}{|} + HOR^3 \xrightarrow[PPh_3]{\overset{NCOOR^5}{\underset{NCOOR^5}{||}}} H_2NSO_2N-R^3\underset{COOR^4}{|}$$

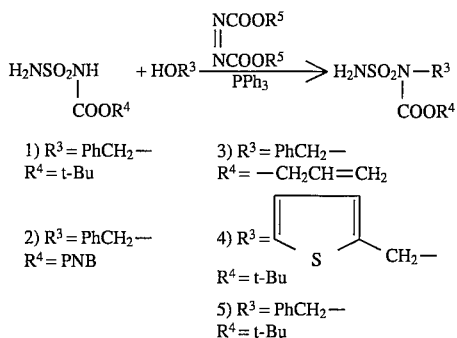

1) $R^3 = PhCH_2-$
  $R^4 = $t-Bu

2) $R^3 = PhCH_2-$
  $R^4 = $PNB

3) $R^3 = PhCH_2-$
  $R^4 = -CH_2CH=CH_2$

4) $R^3 = $ (thienylmethyl)
  $R^4 = $t-Bu

5) $R^3 = PhCH_2-$
  $R^4 = $t-Bu

To a solution of alcohol ($R^3OH$) in a solvent (tetrahydrofuran (THF) or ethyl acetate (EtOAc)) are added triphenylphosphine (or tributylphosphine for Sample No. 5), oxycarbonylsulfamide (OCSD=$R^4OCONHSO_2NH_2$) and either dimethyl azodicarboxylate (DMAD) or diethyl azodicarboxylate (DEAD) under reaction conditions shown in Tables 3 and 4, with the mixture being stirred. The reaction mixture is diluted with water and extracted with a solvent. The extract is dried and concentrated in vacuo to give a sulfamide which is a condensation product of the OSCD and the alcohol. This type of sulfamide is hereinafter referred to as the "condensed sulfamide".

The condensation reaction for producing Sample No. 5 will now be described in detail.

To 103 μl (1 mM) of benzylalcohol dissolved in 4 ml of tetrahydrofuran (THF) is added 294 mg (1.5 mM) of the oxycarbonylsulfamide (OCSD: $R^4$=t-butyl). The mixture is cooled to −60° C. To this mixture are added 294 μl (1.18 mM) of tributylphosphine ((n-Bu)₃P) and 189 μl (1.2 mM) of diethyl azodicarboxylate (DEAD). The mixture is stirred for 2 hours, while gradually raising temperature to room temperature, and then for 40 minutes at that temperature. This reaction mixture is diluted with water and ethyl acetate. The organic layer is washed with water and dried. The solvent is then removed in vacuo. The residue is purified by silica gel chromatography to gave 210 mg of a condensed sulfamide (Yield: 73%) as colorless crystals.

TABLE 3

| | | Condensation (Using benzyl alcohol or thienyl-methyl alcohol) | | | | | |
|---|---|---|---|---|---|---|---|
| Sample No. | THF (vol.)*) | PPh₃ (Eq.) | OCSD (Eq.) | DEAD (Eq.) | Temp. (°C.) | Time (min.) | Yield (%) |
| 1 | 4 | 1.18 | 1.50 | 1.20 | −62 → −45 | 135 | 81 |
| 2 | 4 | 1.18 | 1.50 | 1.20 | −72 → −30 | 300 | 83 |
| 3 | 4 | 1.18 | 1.50 | 1.20 | −52 → −30 | 160 | 90 |
| 4 | 6 | 1.18 | 1.50 | 1.20 | −70 → −60 | 150 | 64 |
| 5 | 4 | 1.18**) | 1.50 | 1.20 | −60 → rt. | 40 | 73 |

Note:
*) A ratio of a solvent (ml) to an alcohol (g).
**) PPh₃ is replaced by n-Bu₃P.

TABLE 4

| | | Condensation (Using benzyl alcohol) | | | | | |
|---|---|---|---|---|---|---|---|
| Sample No. | EtOAc (vol.)*) | PPh₃ (Eq.) | OCSD (Eq.) | DMAD (Eq.) | Temp. (°C.) | Time (min.) | Yield (%) |
| 1 | 4 | 1.20 | 1.50 | 1.20 | −62 → −45 | 30 | 79 |
| 2 | 10 | 1.20 | 1.50 | 1.20 | −72 → −30 | 100 | 81 |

Note:
*) A ratio of a solvent (ml) to an alcohol (g).

Physical constants of the obtained products are as follows:
1) R³=benzyl, R⁴=t-butyl
mp. 130° C.
IR ν (CHCl₃) cm⁻¹: 3410, 3325, 1711, 1372, 1147.
NMR δ (CDCl₃) 200 MHz ppm: 1.48(m, 9H), 4.88(s, 2H), 5.24(s, 2H), 7.21–7.40(m, 5H).
Anal. (C₁₂H₁₈O₄N₂S) Calcd.: C, 50.33; H, 6.33; N, 9.78; S, 11.20. Found: C, 50.27; H, 6.36; N, 9.75; S, 11.03.

2) R³=benzyl, R⁴=p-nitrobenzyl
mp. 128°–129° C.
IR ν (Nujol) cm⁻¹: 3374, 3280, 1711, 1351, 1161.
NMR δ (CD₃SOCD₃) 200 MHz ppm: 4.86(s, 2H), 5.37(s, 2H), 7.20–7.40(m, 5H), 7.53(d, J=8.6 Hz, 2H), 7.96(s, 2H), 8.19(d, J=8.6 Hz, 2H).
Anal. (C₁₅H₁₅O₆N₃S) Calcd.: C, 49.31; H, 4.14; N, 11.50; S, 8.77. Found: C, 49.34; H, 4.23; N, 11.59; S, 8.59.

3) R³=benzyl, R⁴=allyl
mp. 51°–52° C.
IR ν (CHCl₃) cm⁻¹: 3420, 3320, 1716, 1392, 1182.
NMR δ (CDCl₃) 200 MHz ppm: 4.73(d, J=7.4 Hz, 2H), 4.94(s, 2H), 5.26–5.37(m, 4H), 5.81–6.01(m, 1H), 7.26–7.40(m, 5H).
MASS (SIMS) m-NBA m/z: [M+H]⁺ 271.

4) R³=2-thienylmethyl, R⁴=t-butyl
mp. 111°–112° C.
IR ν (CHCl₃) cm⁻¹: 3412, 3315, 1713, 1392, 1148.
NMR δ (CDCl₃) 200 MHz ppm: 1.57(s, 9H), 5.03(s, 2H), 5.14(brs, 2H), 6.97(dd, J₁=3.6 Hz, J₂=5.0 Hz, 1H), 7.11(dd, J₁=1.2 Hz, J₂=3.6 Hz, 1H), 7.26(dd, J₁=1.2 Hz, J₂=4.8 Hz, 1H).
Anal. (C₁₀H₁₆N₄O₂S₂) Calcd.: C, 41.08; H, 5.52; N, 9.58; S, 21.93. Found: C, 40.90; H, 5.59; N, 9.62; S, 21.74.

5) R³=benzyl, R⁴=t-butyl
The obtained physical constants are the same as those obtained in Sample No. 1.

Example 2

(Using pyrrolidinemethanol derivatives)

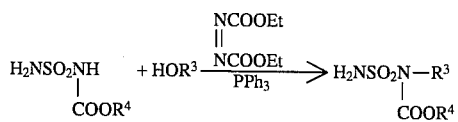

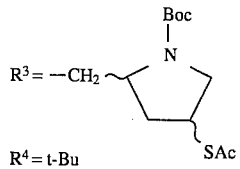

1) 2R4R   2) 2R4S
3) 2S4R   4) 2S4S

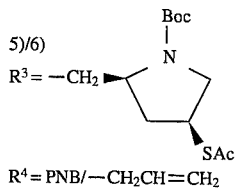

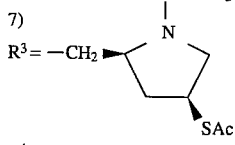

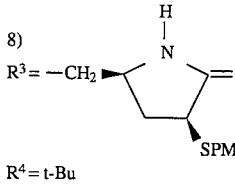

9) 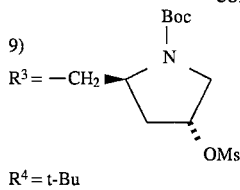

$R^3 = -CH_2$ $R^4 = $ t-Bu

To a solution of a pyrrolidinemethanol derivative ($R^3OH$) in a solvent (tetrahydrofuran (THF), benzene (Bz), ethyl acetate (EtOAc) or toluene (To)) are added triphenylphosphine (PPh$_3$), either diethyl azodicarboxylate (DEAD) or diisopropyl azodicarboxylate (DIPAD), and oxycarbonylsulfamide (OCSD=$R^4OCONHSO_2NH_2$) under reaction conditions as shown in Table 5, with the mixture being stirred. The reaction mixture is concentrated in vacuo to give a condensed sulfamide.

TABLE 5

Condensation (Using pyrrolidinemethanol derivatives)

| Sample No. | Solvent (vol.)*) | PPh$_3$ (Eq.) | OCSD (Eq.) | DEAD (Eq.) | Temp. (°C.) | Time (min.) | Yield (%) |
|---|---|---|---|---|---|---|---|
| 1 | THF | 7 | 1.18 | 1.66 | 1.20 | 0 | 300 | 84 |
| 2 | THF | 20 | 1.34 | 1.20 | 1.30 | 45 | 150 | 76 |
| 3-1 | THF | 10 | 1.28 | 1.50 | 1.30 | rt. | 240 | 82 |
| 3-2 | Bz | 6 | 1.00 | 2.05 | 1.50 | 0 | 100 | 90 |
| 4-1 | EtOAc | 10 | 1.18 | 1.50 | 1.20 | rt. | 300 | 75 |
| 4-2 | THF | 5 | 1.02 | 1.25 | 1.05 | 20 | 240 | 86 |
| 4-3 | THF | 10 | 1.20 | 1.20 | 1.20 | rt. | 60 | 74 |
| 4-4 | To | 7 | 1.02 | 1.00 | 1.00**) | rt. | an.***) | 70 |
| 5 | THF | 14 | 1.18 | 1.50 | 1.20 | 0 | 160 | 38 |
| 6-1 | EtOAc | 50 | 3.50 | 1.50 | 1.20 | rt. | 150 | 67 |
| 6-2 | THF | 10 | 1.20 | 3.72 | 1.20 | rt. | 240 | 63 |
| 6-3 | THF | 10 | 1.20 | 1.50 | 3.50 | rt. | 240 | 60 |
| 6-4 | THF | 14 | 1.20 | 1.50 | 1.20 | rt. | 320 | 69 |
| 7 | EtOAc | 10 | 1.20 | 1.40 | 1.20 | 0 → rt. | 55 → 240 | 55 |
| 8 | THF | 22 | 1.20 | 1.50 | 1.20 | rt. | 210 | 68 |
| 9 | THF | 22 | 1.20 | 1.50 | 1.20 | rt. | 960 | 62 |

Note:
*)A ratio of a solvent (ml) to an alcohol (g).
**)DEAD is replaced by DIPAD (diisopropyl azodicarboxylate).
***)All night.

Physical constants of the obtained products are as follows:
1) $R^3$=(2R,4R)-4-acetylthio-1-t-butoxycarbonylpyrrolidin-2-ylmethyl, $R^4$=t-butyl IR ν (CHCl$_3$) cm$^{-1}$: 3360, 3200, 1710, 1688.

NMR δ (CDCl$_3$) 200 MHz ppm: 1.43(s, 9H), 1.53(s, 9H), 2.34(s, 3H), 2.5(m, 1H), 3.15(dd, J=12.2 Hz, J=6.2 Hz, 1H), 3.58(dd, J=14.8 Mz, J=3.2 Hz, 1H), 3.8–4.1(m, 2H), 4.16(dd, J=12.2 Hz, J=7.8 Hz, 1H), 4.4–4.7(m, 1H), 6.11 (s, 2H).

2) $R^3$=(2R,4S)-4-acetylthio-1-t-butoxycarbonylpyrrolidin-2-ylmethyl, $R^4$=t-butyl IR ν (KBr) cm$^{-1}$: 3420, 3320, 1706, 1686, 1666.

NMR δ (CDCl$_3$) 200 MHz ppm: 1.41(s, 9H), 1.55(s, 9H), 1.9–2.0(m, 2H), 2.35(s, 3H), 3.32(dd, J=11.4 Hz, J=8.2 Hz, 1H), 3.6–3.9(m, 3H), 3.9–4.1 (m, 1H), 4.5(m, 1H), 6.15(s, 2H).

3) $R^3$=(2S,4R)-4-acetylthio-1-t-butoxycarbonylpyrrolidin-2-ylmethyl, $R^4$=t-butyl IR ν (KBr) cm$^{-1}$: 3420, 3320, 1706, 1686, 1666.

NMR δ (CDCl$_3$) 200 MHz ppm: 1.41(s, 9H), 1.55(s, 9H), 1.9–2.0(m, 2H), 2.35(s, 3H), 3.32(dd, J=11.4 Hz, J=8.2 Hz, 1H), 3.6–3.9(m, 3H), 3.9–4.1 (m, 1H), 4.5(m, 1H), 6.15(s, 2H).

4) $R^3$=(2S,4S)-4-acetylthio-1-t-butoxycarbonylpyrrolidin-2-ylmethyl, $R^4$=t-butyl mp. 136°–140° C.

IR ν (CHCl$_3$) cm$^{-1}$: 3380, 3220, 1707, 1696.

NMR δ (CDCl$_3$) 200 MHz ppm: 1.42(s, 9H), 1.53(s, 9H), 2.34(s, 3H), 2.4–2.7(m, 1H), 3.1–3.2(m, 1H), 3.5–4.22(m, 4H), 4.5–4.65(m, 1H), 6.10 (s, 2H).

Anal. (C$_{17}$H$_{31}$N$_3$O$_7$S$_2$) Calcd.: C, 45.01; H, 6.89; N, 9.26; S, 14.14. Found: C, 44.94; H, 6.76; N, 9.22; S, 13.88.

5) $R^3$=(2S,4S)-4-acetylthio-1-t-butoxycarbonylpyrrolidin-2-ylmethyl, $R^4$=p-nitrobenzyl IR ν (CHCl$_3$) cm$^{-1}$: 3370, 3200, 1720, 1686, 1349, 1157.

NMR δ (CDCl$_3$) 200 MHz ppm: 1.41(s, 9H), 2.31(s, 3H), 1.40–2.65(m, 2H), 2.90–4.15(m, 5H), 4.40–4.60(m, 1H), 5.31(dd, J$_1$=15.2 Hz, J$_2$=13.2 Hz, 2H), 6.11(s, 2H), 7.57(d, J=8.6 Hz, 2H), 8.26(d, J=8.6 Hz, 2H).

MASS (SIMS) m-NBA m/z: [M+H]$^+$ 533.

6) $R^3$=(2S,4S )-4-acetylthio-1-t-butoxycarbonylpyrrolidin-2-ylmethyl, $R^4$=allyl IR ν (CHCl$_3$) cm$^{-1}$: 3370, 3250, 1717, 1682, 1394, 1162.

NMR δ (CDCl$_3$) 200 MHz ppm: 1.42(s, 9H), 1.2–1.6 & 2.5–2.7(m, 2H), 3.07–4.15(m, 5H), 4.4–4.6(m, 1H), 4.62–4.71(m, 2H), 5.28–5.44(m, 2H), 5.81–6.05(m, 1H), 6.12(brs, 2H).

MASS (SIMS) m-NBA m/z [M+H]$^+$ 438.

7) $R^3$=(2S,4S)-4-acetylthio-1-allyloxycarbonylpyrrolidin-2-ylmethyl, $R^4$=allyl NMR δ (CDCl$_3$) 200 MHz ppm: 1.5–1.7(m, 1H), 2.35(s, 3H), 2.5–2.7(m, 1H), 3.19 (dd, J=6.3 Hz & 11.5 Hz, 1H), 3.68(dd, J=3.8 Hz & 14.5 Hz, 1H), 3.9–4.3 (m, 3H), 4.3–4.7(m, 5H), 5.2–5.4(m, 4H), 5.8–6.1(m, 4H).

8) $R^3$=(3S,5S)-3-p-methoxybenzylmercapto-2-oxopyrrolidin-5-ylmethyl, $R^4$=t-buyl mp. 132°–134° C.

IR ν (KBr) cm$^{-1}$: 3370, 3345, 3245, 2900, 1695, 1680, 1608.

NMR δ (CD$_3$SOCD$_3$) 200 MHz ppm: 1.5–1.7(m, 1H), 2.45–2.65(m, 1H), 2.8–3.1(m, 2H), 3.2–3.35(m, 1H), 3.35(s, 3H), 3.5–3.7(m, 1H), 3.81, 3.96(ABq, J=12.7 Hz, 2H), 6.61(s, 2H), 6.68(t, J=6.6 Hz, 1H), 6.88, 7.25(2d, J=6.6 Hz, 2H×2), 7.88(s, 1H).

Anal. (C$_{13}$H$_{19}$N$_3$O$_4$S$_2$) Calcd.: C, 45.20; H, 5.54; N, 12.16; S, 18.56. Found: C, 44.97; H, 5.52; N, 12.10; S, 18.34.

9) $R^3$=(2S,4R)-4-methanesulfonyloxy-1-t-butoxycarbonylpyrrolidin-2-ylmethyl, $R^4$=t-butyl mp. 147°–149° C.

IR ν (CHCl$_3$) cm$^{-1}$: 3370, 3210, 1710, 1680.

NMR δ (CDCl$_3$) 200 MHz ppm: 1.44(s, 9H), 1.53(s, 9H), 1.82–2.43(m, 2H), 3.04(s, 3H), 3.4–4.05(m, 4H), 4.55–5.25(m, 2H), 6.04(s, 2H).

Anal. (C$_{16}$H$_{31}$N$_3$O$_9$S$_2$) Calcd.: C, 40.58; H, 6.60; N, 8.87; S, 13.54. Found: C, 40.79; H, 6.55; N, 8.68; S, 13.32.

Example 3

(Using β-lactam alcohol or thienylmethyl alcohol)

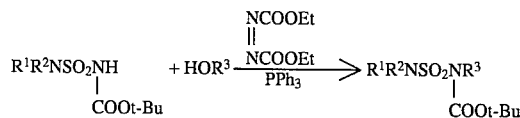

1) $R^1 = R^2 = H$

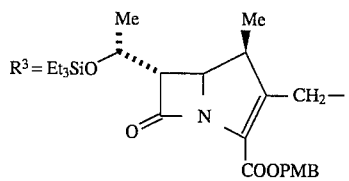

2) $R^1 = Ph$  $R^2 = H$

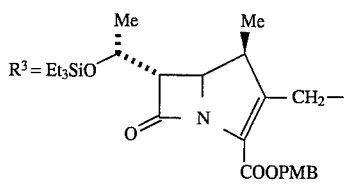

3) $R^1 =$

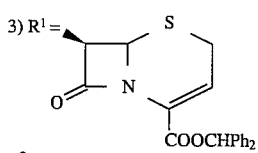

$R^2 = H$ $R^3 =$ 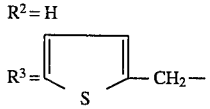

4) $R^1 = R^2 = H$ $R^3 =$

To a solution of alcohol (R$^3$OH) in tetrahydrofuran (THF) are added triphenylphosphine (PPh$_3$), diethyl azodicarboxylate (DEAD) and oxycarbonylsulfamide (OCSD=t-BuOCONHSO$_2$NR$^1$R$^2$) under reaction conditions as shown in Table 6, with the mixture being stirred. The reaction mixture is concentrated in vacuo to give a condensed sulfamide.

TABLE 6

| | Condensation (Using β-lactam alcohol or thionylmethyl alcohol) | | | | | | |
|---|---|---|---|---|---|---|---|
| Sample No. | THF (vol.)*) | PPh$_3$ (Eq.) | OCSD (Eq.) | DEAD (Eq.) | Temp. (°C.) | Time (min.) | Yield (%) |
| 1 | 12 | 1.18 | 1.50 | 1.20 | −60 | 40 | 54 |
| 2 | 12 | 1.18 | 1.50 | 1.20 | −40 | 300 | 58 |
| 3 | 37 | 1.18 | 1.50 | 1.20 | −45 | 135 | 55 |
| 4 | 10 | 1.20 | 1.50 | 1.20 | −70 | 30 | 23 |

Note:
*)A ratio of a solvent (ml) to an alcohol (g).

Physical constants of the obtained products are as follows:
1) $R^1=R^2=H$, $R^3$=((1S,5R,6S)-3-p-methoxybenzyloxycarbonyl-1-methyl-6-[(R)-1-triethylsilyloxyethyl]-carba-2-penem)-2-ylmethyl IR ν (CHCl$_3$) cm$^{-1}$: 3420, 3320, 1771, 1713, 1385, 1145.

NMR δ (CDCl$_3$) 200 MHz ppm: 0.58(q, J=7.4 Hz, 6H), 0.93(t, J=7.4 Hz, 9H), 1.18(d, J=7.4 Hz, 3H), 1.25(d, J=6.2 Hz, 3H), 1.43(s, 9H), 3.17(dq, J$_1$=9.8 Hz, J$_2$=7.4 Hz, 1H), 3.19(dd, J$_1$=6.2 Hz, J$_2$=2.8 Hz, 1H), 3.80(s, 3H), 4.14 (dd, J$_1$=2.8 Hz, J$_2$=9.8 Hz, 1H), 4.23(dq, J$_1$=6.2 Hz, J$_2$=6.2 Hz, 1H), 5.20 & 4.58 (ABq, J$_{AB}$=13.2 Hz, 2H), 5.19(dd, J$_1$=12.2 Hz, J$_2$=15.6 Hz, 2H), 6.88(d, J=8.6 Hz, 2H), 7.37(d, J=8.6 Hz, 2H).

MASS (SIMS) m-NBA m/z: [M+H]$^+$ 654.

2) $R^1$=phenyl, $R^2$=H, $R^3$=((1S,5R,6S)-3-p-methoxybenzyloxycarbonyl-1-methyl-6-[(R)-1-triethylsilyloxyethyl] carba-2-penem)-2-ylmethyl NMR δ (CDCl$_3$) 200 MHz ppm: 0.58(q, J=7.4 Hz, 6H), 0.94(t, J=7.4 Hz, 9H), 0.98(d, J=7.4 Hz, 3H), 1.21(d, J=6.2 Hz, 3H), 1.43(d, J=8.2 Hz, 9H), 2.62(dq, J$_1$=7.4 Hz, J$_2$=9.4 Hz, 1H), 3.09(dd, J$_1$=5.8 Hz, J$_2$=2.8 Hz, 1H), 3.80 (s,3H), 3.86(dd, J$_1$=9.4 Hz, J$_2$=2.8 Hz, 1H), 4.19(dq, J$_1$=6.2 Hz, J$_2$=5.8 Hz, 1H), 4.97 & 4.35(ABq, J$_{AB}$=17.0 Hz, 2H), 5.15(dd, J$_1$=15.6 Hz, J$_2$=12.2 Hz, 2H), 6.86(d, J=9.0 Hz, 2H), 7.14–7.42(m, 7H).

3) $R^1$=(4-diphenylmethoxycarbonyl-3-cephem)-7-yl, $R^2$=H, $R^3$=2-thienylmethyl IR ν (CHCl$_3$) cm$^{-1}$: 3330, 1796, 1726, 1372, 1150.

NMR δ (CDCl$_3$) 200 MHz ppm: 1.61(s, 9H), 3.40, 3.52(d, ABq, 2H, J$_{AB}$=19.4 Hz, J$_1$=2.8 Hz, J$_2$=6.0 Hz), 4.58(d, J=5.2 Hz, 1H), 4.91(dd, J$_1$=5.2 Hz, J$_2$=9.4 Hz, 1H), 5.03(s, 2H), 5.99(d, J=9.4 Hz, 1H), 6.64(dd, J$_1$=2.8 Hz, J$_2$=6.0 Hz, 1H), 6.95(s, 1H), 6.90–7.50(m, 13H).

MASS (SIMS) m-NBA m/z: [M+H]$^+$ 642.

4) $R^1$=$R^2$=H, $R^3$=(4-p-nitrobenzyloxycarbonyl-1-oxo-7-(2-thienylacetamido)-3-cephem)-3-ylmethyl Physical constants were determined after converting to 1-oxide by oxidation in order to move a double bond at the 2-position to the 3-position. The condition for the oxidation is described in Reference Example 14 below.

mp. 138°–142° C.

IR ν (Nujol) cm$^{-1}$: 3360, 3270, 1786, 1725, 1350, 1152.

NMR δ (CD$_3$SOCD$_3$) 200 MHz ppm: 1.41(s, 9H), 3.75 & 3.83(ABq, J$_{AB}$=18.8 Hz,2H), 3.91 & 3.83(ABq, J$_{AB}$=15.4 Hz, 2H), 4.86 & 4.52(ABq, J$_{AB}$=17.2 Hz, 2H), 4.96(d, J=4.6 Hz, 1H), 5.44(dd, J$_1$=14.4 Hz, J$_2$=16.0 Hz, 2H), 5.93(dd, J$_1$=4.6 Hz, J$_2$=8.2 Hz, 1H), 6.94–6.99(m, 2H), 7.38(dd, J$_1$=2.4 Hz, J$_2$=4.4 Hz, 1H), 7.70(s, 2H), 7.72(d, J=8.6 Hz, 2H), 8.25(d, J=8.6 Hz, 2H), 8.47(d, J=8.2 Hz, 1H).

[Condensation using a secondary alcohol]

Example 4

(Using pyrrolidinol)

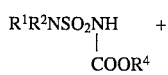

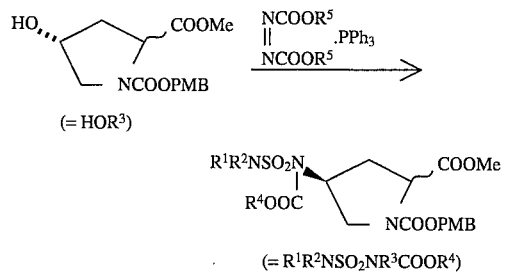

1) 2S.4S  2) 2S.4S  3) 2S.4S  4) 2R.4S
   $R^1$=Ph     $R^1$=H      $R^1$=H      $R^1$=H
   $R^2$=H      $R^2$=H      $R^2$=H      $R^2$=H
   $R^4$=t-Bu   $R^4$=t-Bu   $R^4$=PNB    $R^4$=PNB

To a solution of pyrrolidinol in a solvent (tetrahydrofuran (THF) or ethyl acetate (EtOAc)) are added triphenylphosphine (PPh$_3$), either dimethyl azodicarboxylate (DMAD) or diethyl azodicarboxylate (DEAD), and oxycarbonylsulfamide (OCSD=$R^4$OCONHSO$_2$NR$^1$R$^2$) under reaction conditions shown in Tables 7 and 8, with the mixture being stirred. The reaction mixture is concentrated in vacuo to give a condensed sulfamide having an inverted 4-configuration with respect to the starting material.

TABLE 7

Condensation (Using pyrrolidinol)

| Sample No. | Solvent (vol.)*) | PPh$_3$ (Eq.) | OCSD (Eq.) | DEAD (Eq.) | Temp. (°C.) | Time (min.) | Yield (%) |
|---|---|---|---|---|---|---|---|
| 1-1 | THF (10) | 1.20 | 1.50 | 1.20 | rt. | 300 | 63 |
| 1-2 | EtOAc (10) | 1.20 | 1.50 | 1.20 | rt. | 600 | 33 |
| 2 | THF (15) | 1.20 | 1.30 | 1.20 | rt. | 200 | 26 |
| 3 | THF (11) | 1.10 | 1.15 | 1.10 | rt. | 900 | 24 |

Note;
*) A ratio of a solvent (ml) to an alcohol (g).

TABLE 8

Condensation (Using pyrrolidinol)

| Sample No. | Solvent (vol.)*) | PPh$_3$ (Eq.) | OCSD (Eq.) | DMAD (Eq.) | Te (°C.) | Time (min.) | Yield (%) |
|---|---|---|---|---|---|---|---|
| 3 | THF (15) | 1.38 | 1.40 | 1.20 | rt. | 900 | 23 |
| 4 | THF (15) | 1.20 | 1.50 | 1.20 | rt. | 900 | 36 |

Note:
*) A ratio of a solvent (ml) to an alcohol (g).

Physical constants of the obtained products are as follows:
1) $R^1$=phenyl, $R^2$=H, $R^3$=(2S,4S)-1-(p-methoxybenzyloxycarbonyl)-2-methoxycarbonylpyrrolidin-4-yl, $R^4$=t-butyl IR ν (CHCl$_3$) cm$^{-1}$: 3340, 1745, 1702, 1361, 1144.

NMR δ (CDCl$_3$) 200 MHz ppm: 1.55(s, 9H), 1.81–2.39(m, 2H), 3.00–3.40 (m, 2H), 3.48 & 3.71(2s, 3H), 3.79 & 3.84(2s, 3H), 4.06–4.20(m, 1H), 4.45–4.70(m, 1H), 4.85–5.14(m, 2H), 6.80–6.95(m, 2H), 7.20–7.44 (m, 7H).

MASS (SIMS) m-NBA m/z: [M+H]$^+$ 564.

2) $R^1$=$R^2$=H, $R^3$=(2S,4S)-1-p-methoxybenzyloxycarbonyl-2-methoxycarbonylpyrrolidin-4-yl, $R^4$=t-butyl IR ν (CHCl$_3$) cm$^{-1}$: 3400, 1737, 1700, 1353, 1170.

NMR δ (CDCl$_3$) 200 MHz ppm: 1.43(s, 9H), 1.80–2.56(m, 2H), 3.40–4.85 (m, 8H), 4.21–4.45(m, 2H), 4.92–5.20(m, 2H), 5.20–5.50(brs, 2H), 6.82–6.95(m, 2H), 7.20–7.36(m, 2H)

3) $R^1$=$R^2$=H, $R^3$=(2S,4S)-1-p-methoxybenzyloxycarbonyl-2-methoxycarbonylpyrrolidin-4-yl,
$R^4$=p-nitrobenzyl IR ν (CHCl$_3$) cm$^{-1}$: 3420, 1727, 1348, 1221.

NMR δ (CDCl$_3$) 200 MHz ppm: 1.94–2.60(m, 2H), 3.50–3.85(m, 8H), 4.30–4.50(m, 2H), 4.92–5.21(m, 4H), 6.80–6.92(m, 2H), 7.20–7.34(m, 2H), 7.49(d, J=8.6 Hz, 2H), 8.21(d, J=8.6 Hz, 2H).

4) $R^1$=$R^2$=H, $R^3$=(2R, 4S)-1-p-methoxybenzyloxycarbonyl-2-methoxycarbonylpyrrolidin-4-yl, $R^4$=p-nitrobenzyl IR ν (CHCl$_3$) cm$^{-1}$: 3424, 1701, 1610, 1347, 1122.

NMR δ (CDCl$_3$) 200 MHz ppm: 2.15–2.4(m, 2H), 3.3–3.6(m, 1H), 3.57, 3.76(2×s, 3H), 3.80(s, 3H), 3.7–3.95(m, 1H), 4.25–4.5(m, 2H), 4.9–5.3(m, 5H), 6.8–8.25(m, 8H).

Example 5

(Using a cyclohexanol)

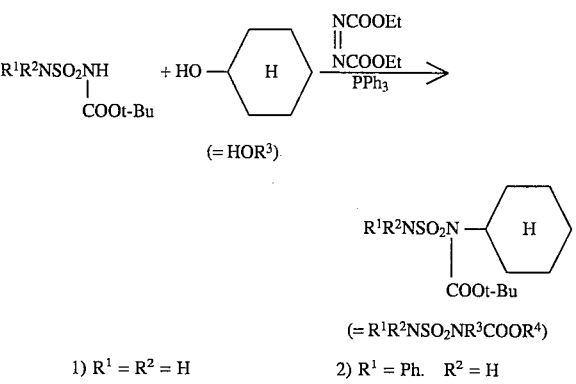

1) $R^1$ = $R^2$ = H    2) $R^1$ = Ph.  $R^2$ = H

To a solution of cyclohexanol in tetrahydrofuran (THF) are added triphenylphosphine (PPh$_3$), diethyl azodicarboxylate (DEAD) and oxycarbonylsulfamide (OCSD=t-BuOCONHSO$_2$NR$^1$R$^2$) under reaction conditions as shown in Table 9, with the mixture being stirred. The reaction mixture is concentrated in vacuo to give a condensed sulfamide.

TABLE 9

Condensation (Using a cyclohexyl alcohol)

| Sample No. | THF (vol.)*) | PPh$_3$ (Eq.) | OCSD (Eq.) | DEAD (Eq.) | Temp. (°C.) | Time (min.) | Yield (%) |
|---|---|---|---|---|---|---|---|
| 1 | 14 | 1.18 | 1.50 | 1.20 | rt. | 300 | 12 |
| 2 | 10 | 1.18 | 1.50 | 1.20 | rt. | 300 | 14 |

Note:
*) A ratio of a solvent (ml) to an alcohol (g).

Physical constants of the obtained products are as follows:
1) $R^1$=$R^2$=H
   mp. 79°–80° C.

IR ν (CHCl₃) cm⁻¹: 3410, 3310, 1701, 1372, 1148.

NMR δ (CDCl₃) 200 MHz ppm: 0.99–2.16(m, 10H), 1.56(s, 9H), 4.15(H, $J_1$=12 Hz, $J_2$=3.6 Hz, 1H), 5.33(s, 2H).

2) R¹=phenyl, R²=H mp. 137°–139° C.

IR ν (CHCl₃) cm⁻¹: 3320, 1702, 1369, 1147.

NMR δ (CDCl₃) 200 MHz ppm: 0.8–1.87(m, 10H), 1.55(s, 9H), 3.84(tt, $J_1$=12.0 Hz, $J_2$=3.6 Hz, 1H), 7.18–7.40(m, 5H).

Anal. ($C_{17}H_{26}N_4O_4S_2$) Calcd.: C, 57.60; H, 7.39; N, 7.90; S, 9.04. Found: C, 57.78; H, 7.42; N, 7.94; S, 8.95.

[Reference Examples]

Reference Example 1

[Deprotection by CF₃COOH]

The condensed sulfamide having a t-butoxycarbonyl protecting group obtained as Sample No. 1 of Example 1 is dissolved in a mixture of dichloromethane (15 vol.) and anisole (15 vol.) under ice cooling, and trifluoroacetic acid (15 vol.) is added thereto. The mixture is stirred for 50 minutes, and for 1 hour after the ice bath is removed. The reaction mixture is concentrated. The residue is recrystallized from a mixture of ether and petroleum ether (1:6) to give benzylsulfamide. Colorless crystals. Yield: 90%.

mp. 107°–108° C.

IR ν (Nujol) cm⁻¹: 3330, 3260, 1336, 1151.

NMR δ (CD₃SOCD₃) 200 MHz ppm: 4.07(d, J=6.4 Hz, 2H), 6.64(s, 2H), 7.09 (t, J=6.4 Hz, 1H), 7.20–7.40(m, 5H).

Anal. ($C_7H_{10}O_2N_2S$) Calcd.: C, 45.14; H, 5.41; N, 15.04; S, 17.22. Found: C, 45.04; H, 5.42; N, 15.12; S, 17.10.

Reference Example 2

[Deprotection by CF₃COOH]

To the condensed sulfamide having a t-butoxycarbonyl protecting group obtained as Sample No. 8 of Example 2 are added anisole (3 vol.) and trifluoroacetic acid (5 vol.). The mixture is stirred at room temperature for 30 minutes and concentrated in vacuo. The residue is recrystalized from dichloromethane to give (3S,5S)-3-p-methoxybenzylmercapto-5-sulfamidomethyl-2-pyrrolidone. Colorless crystals. Yield: 68%.

mp. 132°–134° C.

IR ν (KBr) cm⁻¹: 3370, 3345, 3245, 2900, 1695, 1680, 1608.

NMR δ (CD₃SOCD₃) 200 MHz ppm: 1.5–1.7(m, 1H), 2.45–2.65(m, 1H), 2.8–3.1(m, 2H), 3.2–3.35(m, 1H), 3.35(s, 3H), 3.5–3.7(m, 1H), 3.81, 3.96(ABq, J=12.7 Hz, 2H), 6.61(s, 2H), 6.68(t, J=6.6 Hz, 1H), 6.88, 7.25(2d, J=6.6 Hz, 2H×2), 7.88(s, 1H).

Anal. ($C_{13}H_{19}N_3O_4S_2$) Calcd.: C, 45.20; H, 5.54; N, 12.16; S, 18.56. Found: C, 44.97; H, 5.52; N, 12.10; S, 18.34.

Reference Example 3

[Deprotection by CF₃COOH]

The condensed sulfamide having t-butoxycarbonyl and diphenylmethyl protecting groups obtained as Sample No. 3 of Example 3 is dissolved in a mixture of dichloromethane (6 vol.) and anisole (6 vol.) under ice cooling, and trifluoroacetic acid (6 vol.) is added thereto. The mixture is stirred at room temperature for 90 minutes. The reaction mixture is diluted with ether and petroleum ether which separates 7-[N-(2-thienylmethyl)sulfamoylamino]-3-cephem-4-carboxylic acid as pale yellow powder. Yield: 56%.

mp. 62°–63° C.

IR ν (KBr) cm⁻¹: 3250, 1770, 1715, 1337, 1145.

NMR δ (CD₃OD) 200 MHz ppm: 3.68 & 3.52 (ABX of ABq), (2H, $J_{AB}$=19.2 Hz, $J_{AX}$=2.8 Hz, $J_{BX}$=5.8 Hz), 4.41(dd, $J_1$=15.2 Hz, $J_2$=17.4 Hz, 2H), 5.04(d, J=4.8 Hz, 1H), 5.31(d, J=4.8 Hz, 1H), 6.62(dd, $J_1$=2.8 Hz, $J_2$=5.8 Hz, 1H), 6.95(dd, $J_1$=5.0 Hz, $J_2$=3.4 Hz, 1H), 7.07(dd, $J_1$=3.4 Hz, $J_2$=1.0 Hz, 1H), 7.32(dd, $J_1$=1.2 Hz, $J_2$=5.0 Hz, 1H).

UV λ (MeOH) nm: 235.6 (ε11000).

MIC μg/ml: *S. aureus* JC-1, 6.3; *S. epidermidis*, 3.1.

Reference Example 4

[Deprotection by H₂]

The condensed sulfamide having p-nitrobenzyloxycarbonyl protecting group obtained as Sample No. 2 of Example 1 is dissolved in tetrahydrofuran (10 vol.), and 10% palladium-carbon (0.2 wt %) as a catalyst is added thereto. The mixture is stirred in hydrogen for 1 hour. The catalyst is filtered off, and the filtrate is concentrated in vacuo. The residue is recrystallized from a mixture of ether and petroleum ether to give benzylsulfamide having the same physical constants as that obtained in Reference Example 1. Colorless crystals. Yield: 77%.

Reference Example 5

[Deprotection by H₂]

Similarly to Reference Example 4, p-nitrobenzyl ester obtained in Reference Example 9 described below is hydrogenated in the presence of 10% palladium-carbon to give 7-(2-thienylacetamido)-3-sulfamidomethyl- 3-cephem-4-carboxylic acid. Yield: totally 20% starting from Reference Example 9.

IR ν (Nujol) cm⁻¹: 1755, 1660, 1340, 1150.

NMR δ (D₂O) 200 MHz ppm: 2.76 & 2.96(ABq, $J_{AB}$=17.6 Hz, 2H), 3.16–3.32(m,4H), 4.44(d, J=4.6 Hz, 1H), 4.95(d, J=4.6 Hz, 1H), 6.34–6.41(m, 2H), 6.68–6.73(m, 1H).

UV λ (H₂O) nm: 236 (ε12600).

MIC μg/ml: *S. pyogenes* C-203, 0.1; *S. pneumoniae* I, 0.2.

Reference Example 6

[Deprotection by palladium]

The condensed sulfamide having an allyloxycarbonyl protecting group obtained as Sample No. 3 of Example 1 is dissolved in benzene (10 vol.), and triphenylphosphine (0.3 Eq.), sodium 2-ethylhexanoate (1.5 Eq.) in ethyl acetate, and palladium tetrakistriphenylphosphine (0.02 Eq.) are added thereto successively. The mixture is stirred at room temperature for 30 minutes. The reaction mixture is diluted with ethyl acetate, washed with water, dried, and concentrated in vacuo. The residue is recrystallized from toluene to give benzylsulfamide having the same physical constants as that obtained in Reference Example 1. Pale yellow crystals. Yield: 64%.

Reference Example 7

[Deprotection by AlCl₃]

To a solution of aluminum chloride (6 Eq.) in a mixture of dichloromethane (15 vol.) and anisole (15 vol.) at −55° C. is added a solution of the p-methoxybenzyl ester obtained in Reference Example 13 described below in dichloromethane (7.5 vol.). The mixture is stirred for 25 minutes. The reaction mixture is poured into a solution of sodium acetate (18 Eq.) in water (21 vol.). The aqueous layer is taken, washed with dichloromethane, desalted, and concentrated to give (1S,5R, 6S)-6-[(R)-1-hydroxyethyl]-2-sulfamidomethyl-1-methylcarba-2-penem-3-carboxylic acid as white foam. Yield: 32%.

IR ν (KBr)cm$^{-1}$: 3300, 1745, 1325, 1150.

NMR δ (D$_2$O) 200 MHz ppm: 1.14(d, J=7.4 Hz, 3H), 1.29(d, J=6.2 Hz, 3H), 3.34(dq, J$_1$=7.4 Hz, J$_2$=9.4 Hz, 1H), 3.44(dd, J$_1$=2.4 Hz, J$_2$=6.2 Hz, 1H), 4.19(dd, J$_1$=9.4 Hz, J$_2$=2.4 Hz, 1H), 4.24(dq, J$_1$=6.2 Hz, J$_2$=6.2 Hz, 1H), 4.49 & 3.78(ABq, J$_{AB}$=15.6 Hz, 2H).

UV λ (H$_2$O) nm: 267.4 (ε4500).

MIC μg/ml: *S. pyogenes* C-203, 0.1; *E. coli* EC-14, 0.2.

Reference Example 8

[Deprotection by AlCl$_3$]

Similarly to Reference Example 7, p-methoxybenzyl ester obtained in Reference Example 12 described below is deprotected with aluminum chloride in a mixture of anisole and dichloromethane to give (1S,5R,6S)-6-[(R)-1-hydroxyethyl]-2-(phenylsulfamoylamino)methyl-1-methylcarba-2-penem-3-carboxylic acid. Yield: 22%.

IR ν (KBr) cm$^{-1}$: 1730, 1665, 1405, 1150.

UV λ (MeOH) nm: 227.1 (ε8900), 271.4 (ε4200).

MIC μg/ml: *S. pyogenes* JC-1, 0.2; *S. pneumoniae* I, 0.1.

Reference Example 9

[Deprotection by CF$_3$COOH]

Similarly to Reference Example 1, the condensed sulfamide having a t-butoxycarbonyl protecting group obtained as Sample No. 4 of Example 3 is deprotected with trifluoroacetic acid in a mixture of dichloromethane and anisole to give 7-(2-thienylacetamido)- 3-sulfamidomethyl-3-cephem-4-carboxylic acid p-nitrobenzyl ester. This product is hydrogenated in a manner similar to Reference Example 5 to give the corresponding free acid.

Reference Example 10

[Deprotection by AlCl$_3$]

Similarly to Reference Examples 7 and 8, (1S,5R,6S)-6-[(1R)-1-hydroxyethyl]-2-[(3S,5S)- 5-(N-sulfamoyl-t-butoxycarbonylamino)methylpyrrolidine-3-yl]thio-1-methylcarba-2-penem-3-carboxylic acid diphenylmethyl ester is deprotected with aluminum chloride in a mixture of dichloromethane and anisole to give (1R, 5S,6S)-6-[(1R)-1-hydroxyethyl]-2-[(3S,5S)-5-sulfamidomethylpyrrolidin-3-yl]thio-1-methylcarba-2-penem-3-carboxylic acid.

IR ν (KBr) cm$^{-1}$: 3400, 1750.

MIC μg/ml: *S. aureus* JC-1, <0.003; *S. pyogenes* C-203, <0.003.

Reference Example 11

[Deprotection by NaOMe]

The condensed sulfamide having an acetyl protecting group obtained as Sample No. 4 of Example 2 is dissolved in toluene at −35° C., and a solution of 4.92M sodium methoxide in methanol is added thereto. The mixture is stirred for 30 minutes. The reaction mixture is diluted with water. The aqueous layer is taken, acidified with hydrochloric acid, and extracted with ethyl acetate. The extract is washed with brine and water, dried over sodium sulfate, and concentrated in vacuo. The residue is recrystallized from a mixture of toluene and hexane to give (2S,4S)-1-t-butoxycarbonyl-2-(N-sulfamoyl-t-butoxycarbonylamino)methyl-4-mercaptopyrrolidine. Yield: 69%. Colorless crystals. mp. 92°–93° C.

IR ν (CHCl$_3$) cm$^{-1}$: 3380, 3220, 1718, 1680.

NMR δ (CDCl$_3$) 200 MHz ppm: 1.2–1.5(m, 1H), 1.42(s, 9H), 1.54(s, 9H), 1.82(d, J=6.2 Hz, 1H), 2.5–2.7(m, 1H), 4.09, 3.05(ABX, J=12.0 Hz, J=7.4 Hz, J=8.2 Hz, 2H), 4.06, 3.62(ABX, J=15.0 Hz, J=10.8 Hz, J=3.2 Hz, 2H), 4.2–4.6(m, 1H), 6.08(s, 2H).

Anal. (C$_{15}$H$_{29}$N$_3$O$_6$S$_2$) Calcd.: C, 43.78; H, 7.10; N, 10.21; S, 15.58. Found: C, 43.64; H, 7.10; N, 10.19; S, 15.34.

Reference Example 12

[Deprotection by HCl]

The condensed sulfamide having a triethylsilyl protecting group obtained as Sample No. 2 of Example 3 is dissolved in acetonitrile (14 vol.), and acetic acid (7.5 Eq.) and concentrated hydrochloric acid (15 Eq.) are added thereto at −30° C. The mixture is stirred for 1 hour and 25 minutes. The reaction mixture is poured onto a mixture of aqueous sodium hydrogen carbonate and ethyl acetate. The organic layer is taken, washed with water, dried, and concentrated in vacuo to give (1S,5R,6S)-2-(N-phenylsulfamoyl-N-t-butoxycarbonylamino)methyl-6-[(R)-1-hydroxyethyl]-1-methylcarba-2-penem-3-carboxylic acid p-methoxybenzyl ester. White foam. Yield: 74%.

IR ν (CHCl$_3$) cm$^{-1}$: 3340, 1770, 1715, 1369, 1147.

NMR δ (CDCl$_3$) 200 MHz ppm: 1.03(d, J=7.2 Hz, 3H), 1.29(d, J=6.2 Hz, 3H), 1.42(s, 9H), 2.66(dq, J$_1$=7.2 Hz, J$_2$=8.8 Hz, 1H), 3.15(dd, J$_1$=2.6 Hz, J$_2$=6.2 Hz, 1H), 3.80(s, 3H), 3.88(dd, J$_1$=8.8 Hz, J$_2$=2.6 Hz, 1H), 4.20(dq, J$_1$=6.2 Hz, J$_2$=6.2 Hz, 1H), 4.98 & 4.35(ABq, J$_{AB}$=17.0 Hz, 2H), 5.17(dd, J$_1$=12.2 Hz, J$_2$=23.2 Hz, 2H), 6.87(d, J=9.0 Hz, 2H), 7.12–7.41(m, 9H).

MASS (SIMS) m-NBA m/z: [M+H]$^+$ 616.

Reference Example 13

[Deprotection by HCl]

Similarly to Reference Example 12, the condensed sulfamide having a triethylsilyl protecting group obtained as Sample No. 1 of Example 3 in acetonitrile is desilylated with acetic acid and concentrated hydrochloric acid to give (1S,5R,6S)-2-(N-sulfamoyl-t-butoxycarbonylamino)methyl-6-[(R)-1-hydroxyethyl]-1-methylcarba-2-penem-3-carboxylic acid p-methoxybenzyl ester as white foam. Yield: 79%.

IR ν (CHCl$_3$) cm$^{-1}$: 3420, 1770, 1713, 1369, 1147.

NMR δ (CDCl$_3$) 200 MHz ppm: 1.19(d, J=7.4 Hz, 3H), 1.32(d, J=6.2 Hz, 3H), 1.44(s, 9H), 3.21(dq, J$_1$=9.8 Hz, J$_2$=7.4 Hz, 1H), 3.24(dd, J$_1$=2.8 Hz, J$_2$=6.2 Hz, 1H), 3.80(s, 3H), 4.18(dd, J$_1$=9.8 Hz, J$_2$=2.8 Hz, 1H), 4.23(dq, J$_1$=6.2 Hz, J$_2$=6.2 Hz, 1H), 5.19 & 4.57(ABq, J$_{AB}$=17.2 Hz, 2H), 5.21(dd, J$_1$=12.2 Hz, J$_2$=21.2 Hz, 2H), 5.43(s, 2H), 6.89(d, J=8.6 Hz, 2H), 7.38(d, J=8.6 Hz, 2H)

MASS (SIMS) m-NBA m/z: [M+H]$^+$ 540.

Reference Example 14

[Deprotection by m-CPBA]

The product obtained as Sample No. 4 of Example 3 which has a double bond at the 2-position is dissolved in a mixture of dichloromethane (15 vol.) and methanol (3 vol.) under ice cooling, and 80% m-chloroperbenzoic acid (1.5 Eq.) is added thereto. The mixture is stirred for 30 minutes. The reaction mixture is diluted with dimethylsulfide and ethyl acetate, washed with aqueous sodium hydrogen carbonate and water, dried, and concentrated in vacuo to give 7-(2-thienylacetamido)-3-(N-sulfamoyl-t-butoxycarbonylamino)methyl-3-cephem-4-carboxylic acid p-nitrobenzyl ester.1-oxide as white powder. Yield: 23%. Physical constants of the product are the same as those of Sample No. 4 of Example 3.

Reference Example 15

[Reduction by AcCl-KI]

To a solution of the oxide obtained in Reference Example 14 in acetone (12 vol.) are added potassium iodide (10 Eq.) and acetyl chloride (6 Eq.) at −35° C. The mixture is stirred for 50 minutes. The reaction mixture is washed with aqueous sodium hydrogen carbonate and water and concentrated in vacuo to give 7-(2-thienylacetamido)-3-(N-sulfamoyl-t-butoxycarbonylamino)methyl-3-cephem-4-carboxylic acid p-nitrobenzyl ester as white powder. Yield: 55%.

mp. 108°–124° C.

IR ν (CHCl$_3$) cm$^{-1}$: 3400, 1786, 1722, 1688, 1147.

NMR δ (CDCl$_3$) 200 MHz ppm: 1.51(s, 9H), 3.55, 3.40(ABq, J=18.2 Hz, 2H), 3.86(s, 2H), 5.03, 4.66(ABq, J=16.8 Hz, 2H), 4.96(d, J=4.8 Hz, 1H), 5.32(s, 2H), 5.39(s, 2H), 5.88(dd, J$_1$=4.8 Hz, J$_2$=9.4 Hz, 1H), 6.35(d, J=9.4 Hz, 1H), 6.98–7.30(m, 3H), 7.56, 8.21(2d, J=9.0 Hz, 2H×2).

Anal. (C$_{26}$H$_{29}$O$_{10}$N$_5$S$_3$) Calcd.: C, 46.76; H, 4.37; N, 10.49; S, 14.40. Found: C, 46.70; H, 4.52; N, 10.67; S, 14.37.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a sulfamide, comprising the step of reacting an alcohol and an oxycarbonylsulfamide compound in the presence of a trivalent phosphorus compound and an azodicarboxylic acid derivative, wherein the sulfamide is represented by formula I, the alcohol is represented by Formula II, the oxycarbonylsulfamide compound is represented by Formula III, and the trivalent phosphorus compound is trialkylphosphine, triarylphosphine, or phosphite:

$$R^3NHSO_2NR^1R^2 \qquad (I)$$

wherein R$^1$ and R$^2$ are independently selected from the group consisting of hydrogen, alkyl having 1 to 12 carbon atoms, cycloalkyl having 3 to 9 carbon atoms, alkenyl, alkynyl, aralkyl having 7 to 14 carbon atoms, aryl having 10 or less carbon atoms, a heterocyclic group, and alkyl substituted with the heterocyclic group, respectively, said heterocyclic group being selected from the group consisting of pyranosyl, furanosyl, piperidinyl, pyrrolidinyl, a cephem ring, a penem ring, and a carbapenem ring; R$^3$ is selected from the group consisting of alkyl having 1 to 6 carbon atoms, aralkyl having 7 to 14 carbon atoms, alkyl substituted with a heterocyclic group, and pyrrolidinylmethyl, said heterocyclic group being selected from the group consisting of pyranosyl, furanosyl, piperidinyl, pyrrolidinyl, thienyl, a cephem ring, a penem ring, and a carbapenem ring;

$$R^3OH \qquad (II)$$

wherein R$^3$ is defined as above;

$$R^4OOC-NHSO_2NR^1R^2 \qquad (III)$$

wherein R$^1$ and R$^2$ are defined as above; and R$^4$ is a carboxy protecting group.

2. A method according to claim 1 further comprising the step of removing —COOR$^4$.

3. A method for producing a sulfamide comprising the step of reacting an alcohol and an oxycarbonylsulfamide compound in the presence of a trivalent phosphorus compound and an azodicarboxylic acid derivative, wherein the sulfamide is represented by Formula IV, the alcohol is represented by Formula II, the oxycarbonylsulfamide compound is represented by Formula III, and the trivalent phosphorus compound is trialkylphosphine, triarylphosphine, or phosphite:

$$R^4OOCR^3NSO_2NR^1R^2 \qquad (IV)$$

wherein R$^1$ and R$^2$ are independently selected from the group consisting of hydrogen, alkyl having 1 to 12 carbon atoms, cycloalkyl having 3 to 9 carbon atoms, alkenyl, alkynyl, aralkyl having 7 to 14 carbon atoms, aryl having 10 or less carbon atoms, heterocyclic group, and alkyl substituted with a heterocyclic group, respectively, said heterocyclic group being selected from the group consisting of pyranosyl, furanosyl, piperidinyl, pyrrolidinyl, a cephem ring, a penem ring, and a carbapenem ring; R$^3$ is selected from the group consisting of alkyl having 1 to 6 carbon atoms, aralkyl having 7 to 14 carbon atoms, alkyl substituted with a heterocyclic group, and pyrrolidinylmethyl, said heterocyclic group being selected from the group consisting of pyranosyl, furanosyl, piperidinyl, pyrrolidinyl, thienyl, a cephem ring, a penem ring, and a carbapenem ring; and R$^4$ is a carboxy protecting group;

$$R^3OH \qquad (II)$$

wherein R$^3$ is defined as above;

$$R^4OOC-NHSO_2NR^1R^2 \qquad (III)$$

wherein R$^1$, R$^2$ and R$^4$ are defined as above.

4. The method according to claim 3, wherein R$^1$ and R$^2$ are independently selected from the group consisting of hydrogen, phenyl, and alkyl substituted with a heterocyclic group, respectively, said heterocyclic group being selected from the group consisting of pyranosyl, furanosyl, piperidinyl, pyrrolidinyl, a cephem ring, a penem ring, and a carbapenem ring; R$^3$ is selected from the group consisting of t-butyl, phenylmethyl, aralkyl having 7 to 14 carbon atoms, alkyl substituted with a heterocyclic group, and pyrrolidinylmethyl, said heterocyclic group being selected from the group consisting of pyranosyl, furanosyl, piperidinyl, pyrrolidinyl, thienyl, a cephem ring, a penem ring, and a carbapenem ring; and R$^4$ is a carboxy protecting group.

5. The method according to claim 1, wherein the alcohol is a primary alcohol.

6. The method according to claim 3, wherein the alcohol is a primary alcohol.

7. The method according to claim 4, wherein the alcohol is a primary alcohol.

8. The method according to claim 1, wherein the trivalent phosphorous compound is triethylphosphine, tributylphosphine, triphenylphoshine, tritolylphosphine, methyl phosphite, ethyl phosphite or phenyl phosphite.

9. The method according to claim 3, wherein the trivalent phosphorous compound is triethylphosphine, tributylphosphine, triphenylphoshine, tritolylphosphine, methyl phosphite, ethyl phosphite or phenyl phosphite.

10. The method according to claim 4, wherein the trivalent phosphorous compound is triethylphosphine, tributylphosphine, triphenylphoshine, tritolylphosphine, methyl phosphite, ethyl phosphite or phenyl phosphite.

11. The method according to claim 1, wherein the azodicarboxylic acid derivative is alkyl azodicarboxylate, azodicarboxamide, bisdialkylamide of azodicarboxylic acid or 1,1'-(azodicarbonyl)dialkyleneamine.

12. The method according to claim 3, wherein the azodicarboxylic acid derivative is alkyl azodicarboxylate, azodicarboxamide, bisdialkylamide of azodicarboxylic acid or 1,1'-(azodicarbonyl)dialkyleneamine.

13. The method according to claim 4, wherein the azodicarboxylic acid derivative is alkyl azodicarboxylate, azodicarboxamide, bisdialkylamide of azodicarboxylic acid or 1,1'-(azodicarbonyl)dialkyleneamine.

14. The method according to claim 1, wherein the azodicarboxylic acid derivative is methyl azodicarboxylate, ethyl azodicarboxylate, isopropyl azodicarboxylate, azodinitrile, azodicarboxamide, bisdimethylamide of azodicarboxylic acid, bisdiethylamide of azodicarboxylic acid, 1,1'-(azodicarbonyl)dipyrrolidine and 1,1'-(azodicarbonyl)dipiperidine.

15. The method according to claim 3, wherein the azodicarboxylic acid derivative is methyl azodicarboxylate, ethyl azodicarboxylate, isopropyl azodicarboxylate, azodinitrile, azodicarboxamide, bisdimethylamide of azodicarboxylic acid, bisdiethylamide of azodicarboxylic acid, 1,1'-(azodicarbonyl)dipyrrolidine and 1,1'-(azodicarbonyl)dipiperidine.

16. The method according to claim 4, wherein the azodicarboxylic acid derivative is methyl azodicarboxylate, ethyl azodicarboxylate, isopropyl azodicarboxylate, azodinitrile, azodicarboxamide, bisdimethylamide of azodicarboxylic acid, bisdiethylamide of azodicarboxylic acid, 1,1'-(azodicarbonyl)dipyrrolidine and 1,1'-(azodicarbonyl)dipiperidine.

17. The method according to claim 3,
wherein $R^1$ and $R^2$ are independently selected from the group consisting of hydrogen, phenyl, paranitrobenzyl, benzyl and alkyl substituted with a heterocyclic group, said heterocyclic group consisting of cephem ring, and a carbapenem ring; $R^3$ is selected from the group consisting of t-butyl, phenylmethyl, pyrrolidinylmethyl, thienylmethyl, methyl substituted with a cephem ring, and methyl substituted with a carbapenem ring; and $R^4$ is a carboxy protecting group.

* * * * *

UNITED STATES PATENT AND TRADEMARK OFFICE
CERTIFICATE OF CORRECTION

PATENT NO.   : 5,539,102

DATED        : July 23, 1996

INVENTOR(S)  : Yuji Sendo et al

It is certified that error appears in the above-identified patent and that said Letters Patent is hereby corrected as shown below:

Column 1, line 55, insert --;-- between "ring" and "$R^3$".

Column 2, line 60, change "caphem" to --cephem--.

Column 3, line 4, change "end" to --and--.

Column 3, line 12, change "end" to --and--.

Column 3, line 17, change "caphem" to --cephem--.

Column 3, line 21, change "aralyl" to --aralkyl--.

Column 3, line 27, change "caphem" to --cephem--.

Column 3, line 55, change "cyolopentyl" to --cyclopentyl--.

Column 6, line 8, change "penem3" to --penem-3--.

Column 8, line 25, below the chemical equation of Example 1, insert --$R^5$ = Me / Et--.

Column 9, line 32, change "m" to --s--.

Column 11, line 50, change "Mz" to --Hz--.

UNITED STATES PATENT AND TRADEMARK OFFICE
CERTIFICATE OF CORRECTION

PATENT NO.    : 5,539,102

DATED         : July 23, 1996

INVENTOR(S)   : Yuji Sendo et al

It is certified that error appears in the above-identified patent and that said Letters Patent is hereby corrected as shown below:

Column 12, line 56, change "buyl" to --butyl--.

Column 14, line 5, in the heading for Table 6, change "thionylmethyl" to --thienylmethyl--.

Column 15, line 54, in the legend for Table 8, change "Te" to --Temp.--.

Column 17, line 3, change "H" to --tt--.

Signed and Sealed this

Seventeenth Day of June, 1997

BRUCE LEHMAN

*Attest:*

*Attesting Officer*          Commissioner of Patents and Trademarks